(12) United States Patent
Ryan et al.

(10) Patent No.: US 9,820,660 B2
(45) Date of Patent: Nov. 21, 2017

(54) DEVICES, SYSTEMS, AND METHODS FOR ASSESSING A VESSEL WITH OPTIMIZED PROXIMAL AND DISTAL PRESSURE MEASUREMENTS OBTAINED WITHOUT THE USE OF A HYPEREMIC AGENT

(71) Applicant: Volcano Corporation, San Diego, CA (US)

(72) Inventors: S. Eric Ryan, San Diego, CA (US); Fergus Merritt, El Dorado Hills, CA (US)

(73) Assignee: VOLCANO CORPORATION, San Diego, CA (US)

( * ) Notice: Subject to any disclaimer, the term of this patent is extended or adjusted under 35 U.S.C. 154(b) by 428 days.

(21) Appl. No.: 14/518,217

(22) Filed: Oct. 20, 2014

(65) Prior Publication Data
US 2015/0112152 A1 Apr. 23, 2015

Related U.S. Application Data

(60) Provisional application No. 61/893,019, filed on Oct. 18, 2013.

(51) Int. Cl.
*A61B 5/0215* (2006.01)
*A61B 5/02* (2006.01)
*A61B 5/0452* (2006.01)

(52) U.S. Cl.
CPC ........ *A61B 5/0215* (2013.01); *A61B 5/02007* (2013.01); *A61B 5/02158* (2013.01); *A61B 5/04525* (2013.01)

(58) Field of Classification Search
CPC .................................................. A61B 5/0215
See application file for complete search history.

(56) References Cited

U.S. PATENT DOCUMENTS

| 6,767,327 | B1* | 7/2004 | Corl | A61B 5/0215 |
| | | | | 600/486 |
| 2007/0270700 | A1 | 11/2007 | Hung | |
| 2011/0066047 | A1 | 3/2011 | Belleville et al. | |
| 2012/0179055 | A1 | 7/2012 | Tamil et al. | |
| 2013/0046190 | A1* | 2/2013 | Davies | A61B 5/0215 |
| | | | | 600/486 |
| 2013/0190633 | A1* | 7/2013 | Dorando | A61B 5/02158 |
| | | | | 600/486 |

FOREIGN PATENT DOCUMENTS

WO WO 2012/093260 A1 7/2012
WO WO 2012/093266 A1 7/2012

OTHER PUBLICATIONS

International Searching Authority/United States Patent Office, "Notification of Transmittal of the International Search Report and the Written Opinion of the International Searching Authority, or the Declaration," for PCT/US2014/061090, dated Jan. 27, 2015, 11 pages.

* cited by examiner

*Primary Examiner* — John R Downey

(57) ABSTRACT

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries without the administration of a hyperemic agent. In some embodiments, the devices, systems, and methods of the present disclosure are configured to optimize proximal and distal pressure measurements utilized to assess the vessel.

20 Claims, 9 Drawing Sheets

DEVICES, SYSTEMS, AND METHODS FOR ASSESSING A VESSEL WITH OPTIMIZED PROXIMAL AND DISTAL PRESSURE MEASUREMENTS OBTAINED WITHOUT THE USE OF A HYPEREMIC AGENT

CROSS-REFERENCE TO RELATED APPLICATION

The present application claims the benefit of the filing date of U.S. Provisional Application No. 61/893,019 filed Oct. 18, 2013. The entire disclosure of this provisional application is incorporated herein by this reference.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents.

SUMMARY

Embodiments of the present disclosure are configured to assess the severity of a blockage in a vessel and, in particular, a stenosis in a blood vessel without the administration of a hyperemic agent by optimizing the proximal and distal pressure measurements utilized to assess the vessel.

In some embodiments, a method of evaluating a vessel of a patient are provided. The method can include obtaining proximal pressure measurements measured at a position proximal of a stenosis of the vessel for a plurality of heartbeat cycles; obtaining distal pressure measurements measured at a position distal of the stenosis of the vessel for the plurality of heartbeat cycles; evaluating the obtained proximal and distal pressure measurements to identify any irregular heartbeat cycles within the plurality of heartbeat cycles; optimizing the obtained proximal and distal pressure measurements by removing pressure measurements associated with the irregular heartbeat cycles; calculating a pressure ratio between the optimized distal pressure measurements and the optimized proximal pressure measurements; and outputting the calculated pressure ratio to a display. The calculated pressure ratio can be output to the display in real time. In some implementations, the proximal pressure measurements are obtained from a pressure-sensing catheter, while the distal pressure measurements are obtained from a pressure-sensing guidewire.

In some instances, the obtained proximal and distal pressure measurements are compared to a library of pressure measurements associated with normal heartbeat cycles to identify any irregular heartbeat cycles within the plurality of heartbeat cycles. In some instances, the obtained proximal and distal pressure measurements for one heartbeat cycle of the plurality of heartbeat cycles are compared to the obtained proximal and distal pressure measurements for other heartbeat cycles of the plurality of heartbeat cycles to identify any irregular heartbeat cycles within the plurality of heartbeat cycles.

In some implementations, the method further includes obtaining ECG signals for the plurality of heartbeat cycles and evaluating the obtained ECG signals to identify any irregular heartbeat cycles within the plurality of heartbeat cycles. In that regard, evaluating the obtained ECG signals to identify any irregular heartbeat cycles within the plurality of heartbeat cycles can include comparing the obtained ECG signals to a library of ECG signals associated with normal heartbeat cycles or comparing the obtained ECG signals for one heartbeat cycle of the plurality of heartbeat cycles to the obtained ECG signals for other heartbeat cycles of the plurality of heartbeat cycles.

Systems specifically configured to implement such methods are also provided.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
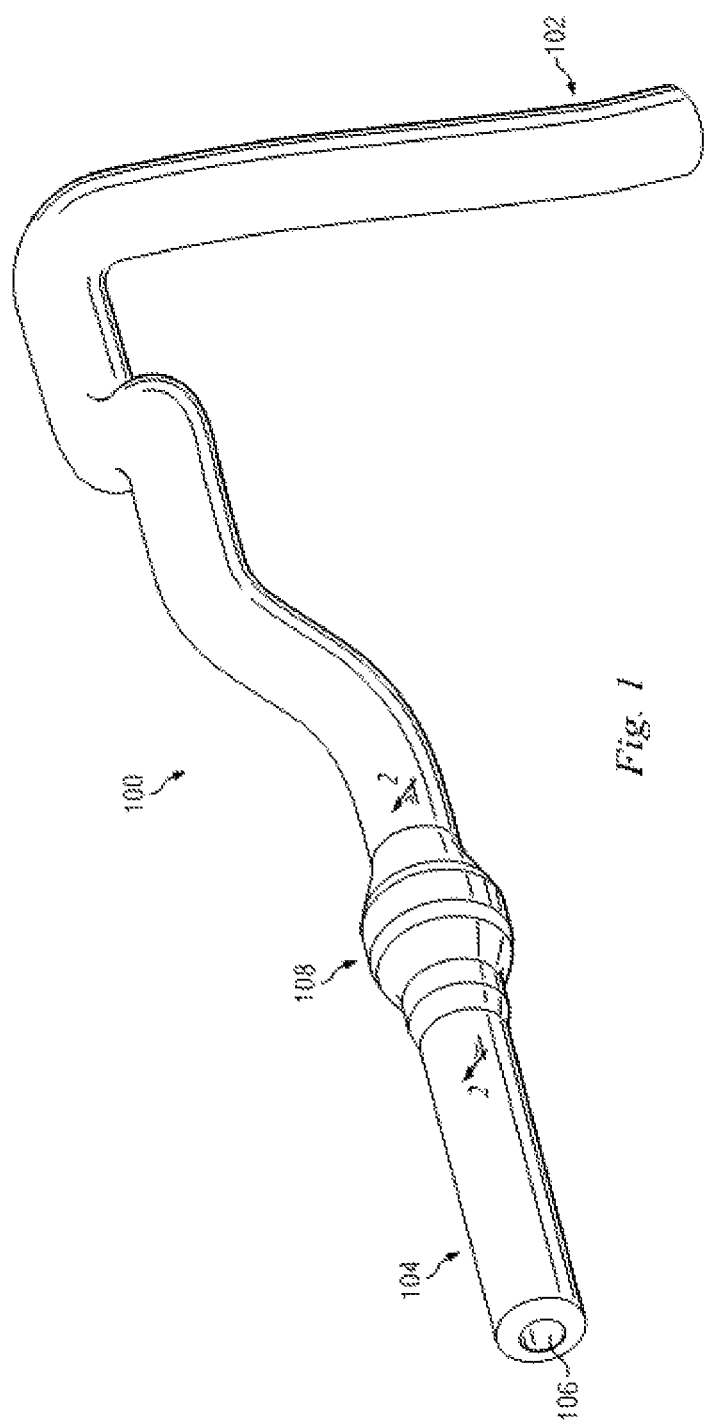
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
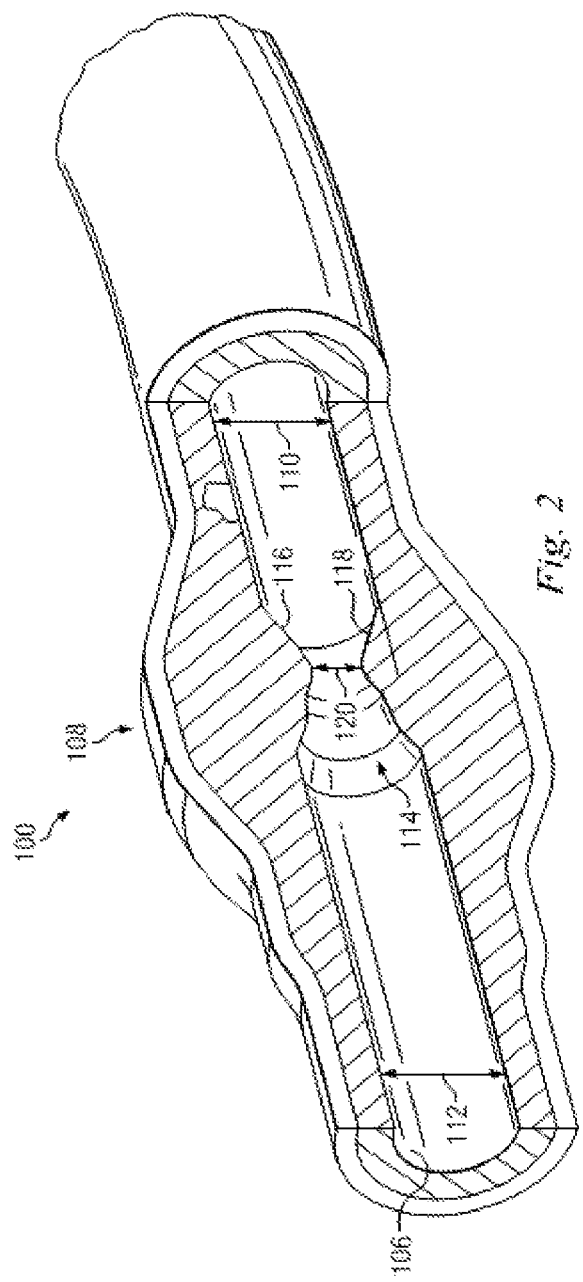
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a systemic blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
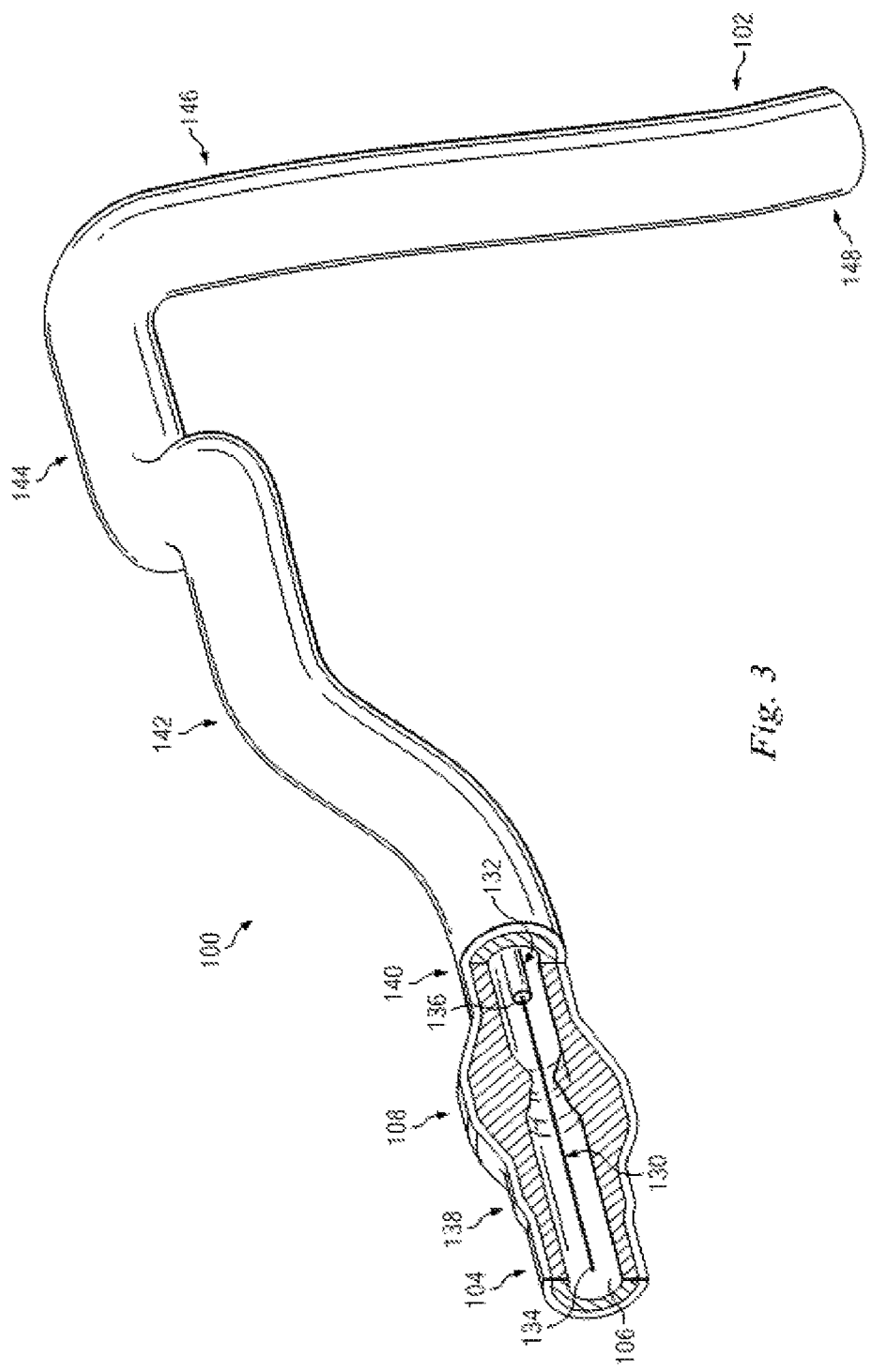
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In that regard, the single instrument incorporates aspects of the functionalities (e.g., data acquisition) of both instruments 130 and 132 in some embodiments.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Millar catheters are utilized in some embodiments.

Currently available catheter products suitable for use with one or more of Philips's Xper™ Flex Cardio Physiomonitoring System, GE's Mac-Lab™ XT and XTi hemodynamic recording systems, Siemens's AXIOM Sensis XP® VC11, McKesson's Horizon Cardiology™ Hemo, and Mennen's Horizon XVu Hemodynamic Monitoring System and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

Figure 4:
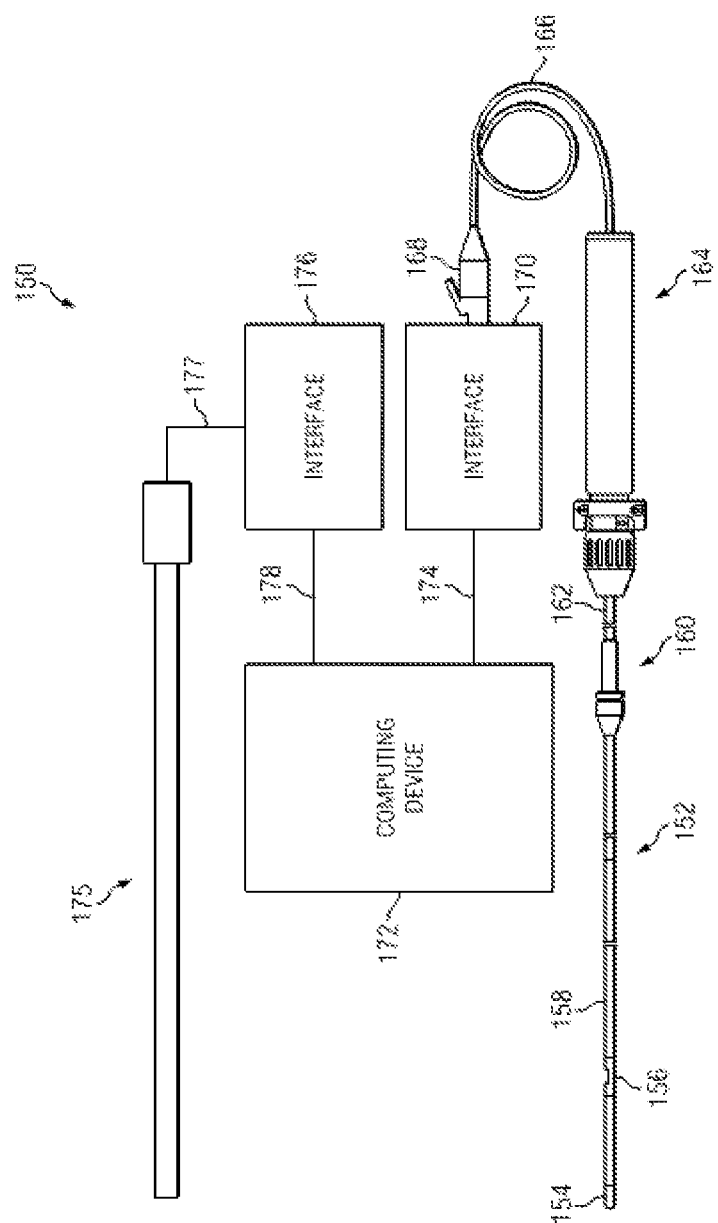
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis®, Mennen Horizon XVu, and Philips Xper™ IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Figure 5:
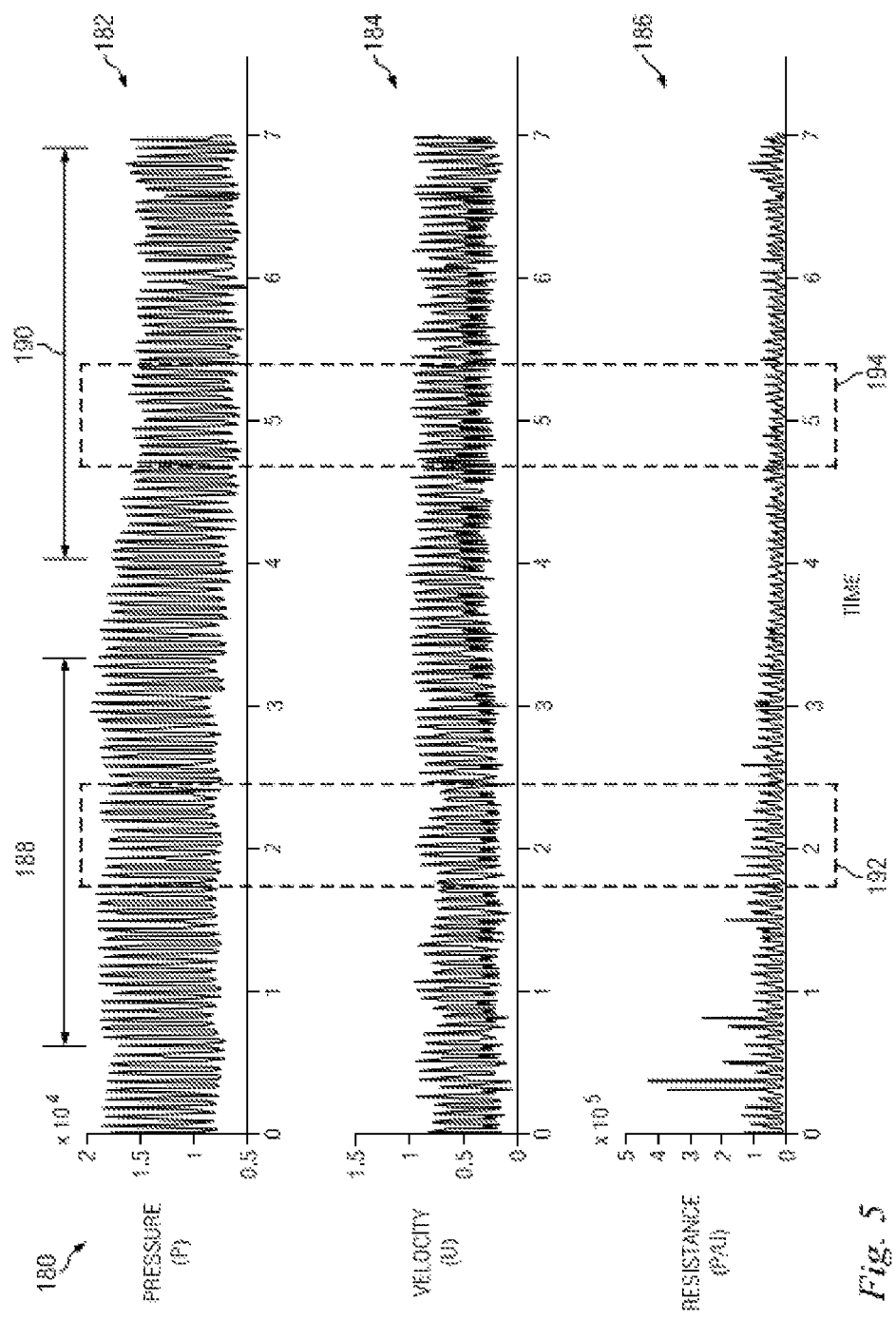
FIG. 5 is a graphical representation of measured pressure, velocity, and resistance within a vessel according to an embodiment of the present disclosure.
Figure 6:
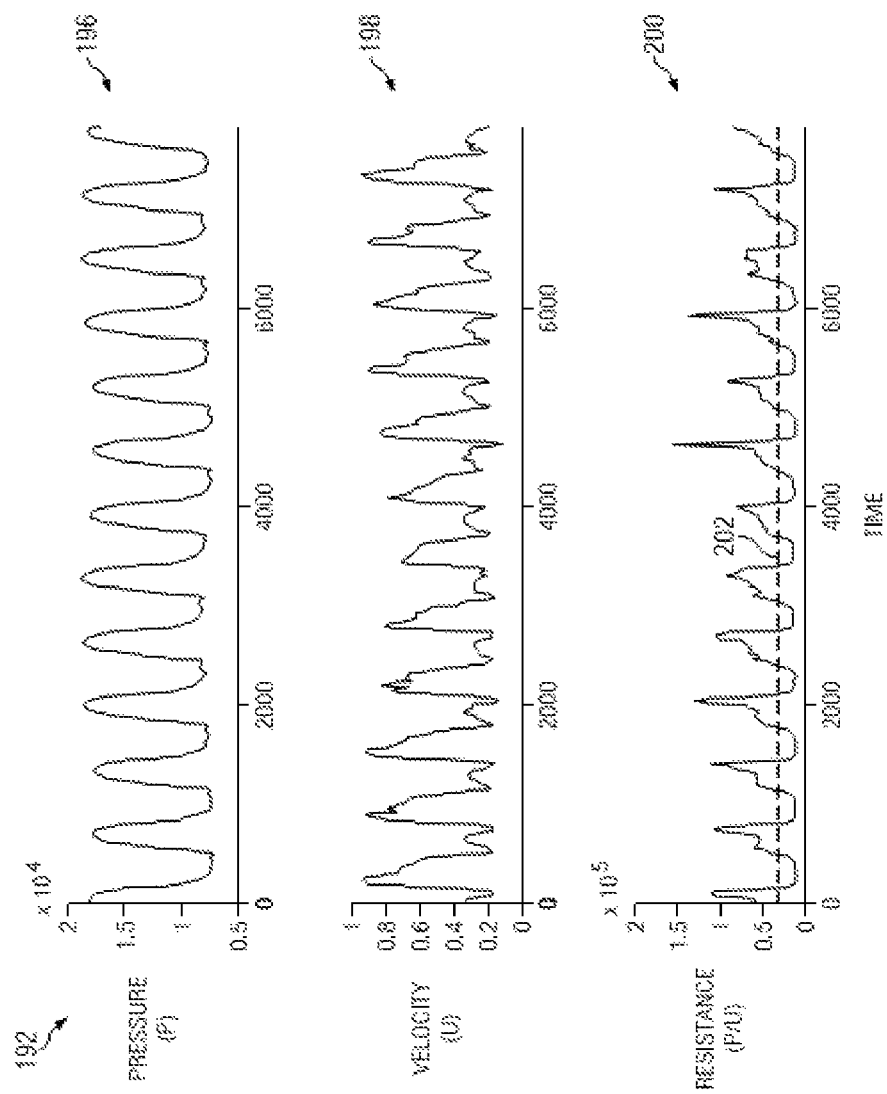
FIG. 6 is a magnified view of a portion of the graphical representation of FIG. 5 corresponding to a resting state of a patient.
Figure 7:
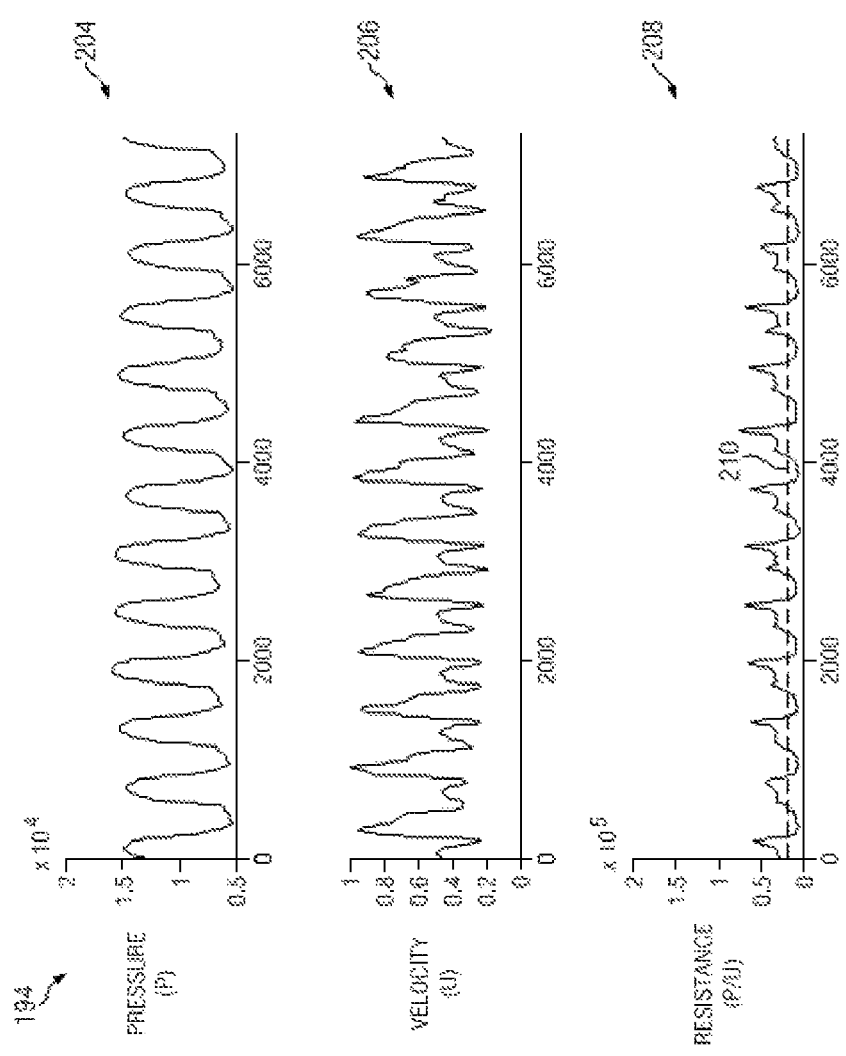
FIG. 7 is a magnified view of a portion of the graphical representation of FIG. 5 corresponding to a hyperemic state of a patient.

Referring now to FIGS. 5-7, shown therein are graphical representations of diagnostic information illustrating aspects of an embodiment of the present disclosure. In that regard, FIG. 5 is a graphical representation of measured pressure, velocity, and resistance within a vessel; FIG. 6 is a magnified view of a portion of the graphical representation of FIG. 5 corresponding to a resting state of a patient; and FIG. 7 is a magnified view of a portion of the graphical representation of FIG. 5 corresponding to a hyperemic state of a patient.

Referring more particularly to FIG. 5, shown therein is a graphical representation 180 of diagnostic information pertaining to a vessel. More specifically, the graphical representation 180 includes a graph 182 plotting pressure within the vessel over time, a graph 184 plotting velocity of the fluid within the vessel over time, and a graph 186 plotting resistance within the vessel over time. In that regard, the resistance (or impedance) shown in graph 186 is calculated based on the pressure and velocity data of graphs 182 and 184. In particular, the resistance values shown in graph 186 are determined by dividing the pressure measurement of graph 182 by the velocity measurement 184 for the corresponding point in time. The graphical representation 180 includes a time period 188 that corresponds to a resting state of the patient's heart and a time period 190 that corresponds to a stressed state of the patient's heart. In that regard, the stressed state of the patient's heart is caused by the administration of a hyperemic agent in some instances.

To better illustrate the differences in the pressure, velocity, and resistance data between the resting and stressed states of the patient, close-up views of the data within windows 192 and 194 are provided in FIGS. 6 and 7. Referring more specifically to FIG. 6, window 192 of the graphical representation 180 includes graph portions 196, 198, and 200 that correspond to graphs 182, 184, and 186, respectively. As shown, in the resting state of FIG. 6, the resistance within the vessel has an average value of approximately 0.35 on the scale of graph 200, as indicated by line 202. Referring now to FIG. 7, window 194 of the graphical representation 180 includes graph portions 204, 206, and 208 that correspond to graphs 182, 184, and 186, respectively. As shown, in the stressed state of FIG. 7, the resistance within the vessel is significantly less than the resting state with a value of approximately 0.20 on the scale of graph 208, as indicated by line 210. As current FFR techniques rely on the average pressures across an entire heartbeat cycle, it is necessary to stress the patient's heart to achieve this reduced and relatively constant resistance across the entire heartbeat so that the data obtained is suitable for use with FFR techniques.

In some previous patent applications, making pressure ratio calculations over a diagnostic window encompassing only a portion of the heartbeat cycle has been utilized to evaluate a stenosis of a vessel of a patient without the use of a hyperemic agent or other stressing of the patient's heart. In some instances, these pressure ratio calculations made without the use of a hyperemic agent and encompassing only a portion of the heartbeat cycle have been referred to as an "iFR" calculation. Each of the following applications disclose related techniques U.S. Patent Publication No. 2013/0046190 A1, published on Feb. 21, 2013 and titled "DEVICES, SYSTEMS, AND METHODS FOR ASSESSING A VESSEL," International Publication No. WO 2012/093266 A1, published Jul. 12, 2012 and titled "APPARATUS AND METHOD OF ASSESSING A NARROWING IN A FLUID FILLED TUBE," and International Publication No. WO 2012/093260 A1, published on Jul. 12, 2012 and titled "APPARATUS AND METHOD OF CHARACTERIZING A NARROWING IN A FLUID FILLED TUBE," each of which is hereby incorporated by reference in its entirety.

The present disclosure provides techniques for evaluating the functional significance of a vessel lesion without the use of a hyperemic agent by optimizing or filtering the proximal and distal pressure measurements that are utilized for calculating a pressure ratio across the stenosis. In that regard, the optimization of proximal and distal pressure measurements may be accomplished by evaluating characteristics and/or components of one or more of proximal pressure measurements, distal pressure measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, ECG waveforms, and/or other identifiable and/or measurable aspects of vessel performance to filter out abnormal or outlier heartbeat cycles such that only suitable proximal and distal pressure measurements are utilized in calculating the pressure ratio across the lesion. By optimizing the proximal and distal pressure measurements in this manner, the correlation of these traditionally raw pressure ratio calculations to FFR and/or iFR measurements can be greatly enhanced. As a result of this enhanced correlation, the optimized pressure ratio calculations can now provide the surgeon or other user of the system valuable insight as to the severity of the lesion(s) within a vessel without the need for FFR and/or iFR measurements or in combination with FFR and/or iFR measurements.

In some embodiments, the optimization of the proximal and distal pressure measurements and/or the calculation of the pressure ratio are performed in approximately real time or live. In that regard, calculating the pressure ratio in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure ratio calculation is performed 10 or more seconds after data acquisition. For example, in some embodiments, the data utilized to identify the diagnostic window and/or calculate the pressure ratio are stored for later analysis.

Because the pressure ratio can be calculated based on a single cardiac cycle in accordance with the present disclosure, a real-time or live pressure ratio calculation can made while the distal pressure measuring device is moved through the vessel (e.g., during a pullback). Accordingly, in some instances the system includes at least two modes: a single-cardiac-cycle mode that facilitates pressure ratio calculations while moving the distal pressure measuring device through the vessel and a multi-cardiac-cycle mode that provides a more precise pressure ratio calculation at a discrete location. In one embodiment of such a system, the software user interface is configured to provide the live pressure ratio value until the distal pressure measuring device is moved to the desired location and a measurement button is selected and/or some other actuation step is taken to trigger the multi-cardiac-cycle mode calculation.

Figure 8:
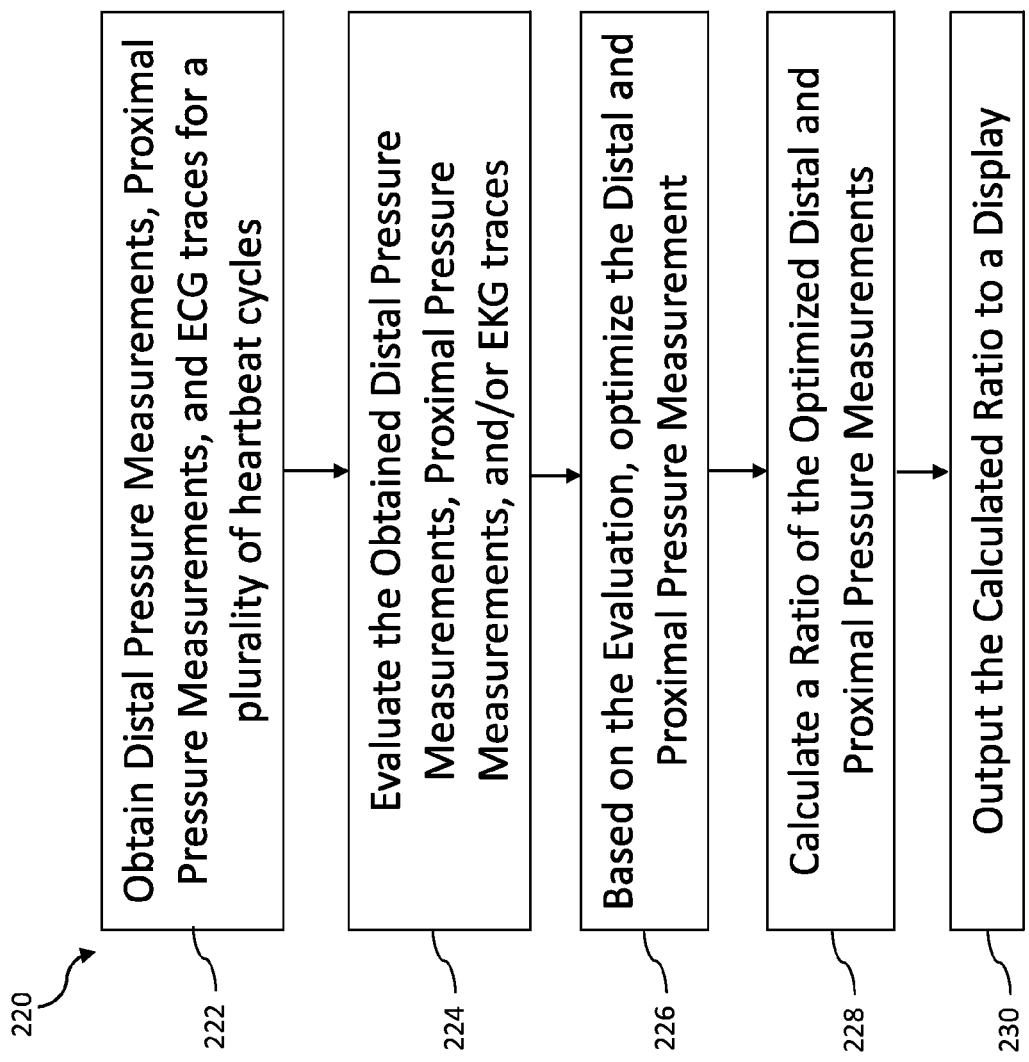
FIG. 8 is a flow chart illustrating steps of a method for evaluating a vessel according to an embodiment of the present disclosure.

Referring now to FIG. 8, shown therein is a flow chart illustrating steps of a method 220 for evaluating a vessel according to an embodiment of the present disclosure. At step 222, the method begins with obtaining distal pressure measurements, proximal pressure measurements, and ECG traces for a plurality of heartbeat cycles. In some implementations, the distal pressure measurements are obtained with a pressure-sensing guidewire, while the proximal pressure measurements are obtained with a pressure-sensing catheter. In some implementations, the ECG traces are obtained using a 12-lead ECG device or other suitable ECG device. Further, the distal and proximal pressure measurements and the ECG traces can be obtained in real time or on a delayed basis. For example, in some implementations one or more of the distal pressure measurements, the proximal pressure measurements, and the ECG traces are obtained during a live procedure. In other instances, one or more of the distal pressure measurements, the proximal pressure measurements, and the ECG traces are obtained from one or more databases, hard drives, memories, or other storage devices containing data related to a previously performed procedure.

At step 224, the method 220 continues with the evaluation of the obtained distal pressure measurements, proximal pressure measurements, and/or ECG traces. In particular, the obtained distal pressure measurements, proximal pressure measurements, and/or ECG traces are evaluated to identify any irregular heartbeat cycles within the plurality of heartbeat cycles for which data was obtained. In that regard, the irregular heartbeat cycles are identified based on the characteristics of the associated distal pressure measurements, proximal pressure measurements, and/or ECG traces.

For example, the ECG traces can be compared to a library of ECG traces for normal heartbeat cycles. If an ECG trace does not match one of the normal ECG traces in the library, then the heartbeat cycle associated with that ECG trace is identified or tagged as an irregular heartbeat cycle. It is understood that the library of ECG traces may be selected based on patient characteristics, recognizing that a "normal" ECG trace for a heartbeat cycle can be different as a result of a particular patient's circumstances or conditions. Likewise, the library of ECG traces can include examples of irregular heartbeat cycles such that if the ECG trace matches an irregular heartbeat cycle trace it is identified or tagged as such. The evaluation of whether an ECG trace matches (or does not match) an ECG trace from the library can be determined using any suitable mathematical data evaluation techniques, including without limitation partial least squares regression, linear regression, non-linear regression, and/or other comparative analysis techniques.

Further, the threshold for determining how close (or far away) an ECG trace must be to an ECG trace from the library to be considered a match (or not a match) can be selected based on user preference, empirical results, and/or a combination thereof. In some implementations, to be considered a match the ECG trace must deviate from an ECG trace of the library by less than 30%, less than 20%, less than 10%, less than 5%, less than 3%, or less than 1%. Similarly, in some implementations, to be considered not a match the ECG trace must deviate from an ECG trace of the library by more than 30%, more than 20%, more than 10%, more than 5%, more than 3%, or more than 1%.

In some instances, the ECG trace is compared to objective measurement criteria to determine whether the associated heartbeat cycle is to be considered normal or irregular. For example, in some implementations heart rate can be used to evaluate the ECG trace. If the heart rate is faster or slower than a normal range, then the corresponding heartbeat cycle (s) can be considered irregular. In some instances, a heartbeat cycle is considered to be slower than normal and, therefore, irregular if the heart rate is less than 40 beats per minute, less than 30 beats per minute, or less than 20 beats per minute. In some instances, a heartbeat cycle is considered to be faster than normal and, therefore, irregular if the heart rate is greater than 160 beats per minute, greater than 180 beats per minute, or greater than 200 beats per minute.

Similar matching and comparison approaches may be utilized for the distal pressure measurements and/or the proximal pressure measurements. That is, the waveforms for the obtained distal and proximal pressure measurements can be compared to a library of distal and proximal pressure measurement waveforms, respectively, for normal heartbeat cycles. If a pressure measurement waveform does not match one of the normal pressure measurement waveforms in the library, then the heartbeat cycle associated with that pressure measurement is identified or tagged as an irregular heartbeat cycle. It is understood that the library of pressure waveforms may be selected based on patient characteristics, recognizing that a "normal" pressure waveform for a heartbeat cycle can be different as a result of a particular patient's circumstances or conditions. Likewise, the library of pressure waveforms can include examples of irregular heartbeat cycles such that if the pressure waveform matches an irregular heartbeat cycle waveform it is identified or tagged as such. The evaluation of whether a pressure waveform matches (or does not match) a pressure waveform from the library can be determined using any suitable mathematical data evaluation techniques, including without limitation partial least squares regression, linear regression, non-linear regression, and/or other comparative analysis techniques.

Further, the distal pressure measurements, proximal pressure measurements, and/or ECG traces can be compared to the other distal pressure measurements, proximal pressure measurements, and/or ECG traces obtained in step 222. In that regard, if the distal pressure measurement, proximal pressure measurement, and/or ECG trace deviates too far from the other distal pressure measurements, proximal pressure measurements, and/or ECG traces, respectively, then the heartbeat associated with that distal pressure measurement, proximal pressure measurement, and/or ECG trace can be considered an irregular heartbeat cycle. The evaluation of whether the distal pressure measurement, proximal pressure measurement, and/or ECG trace deviates too far from the other distal pressure measurements, proximal pressure measurements, and/or ECG traces, respectively, can be determined using any suitable mathematical data evaluation techniques, including without limitation deviation from the mean, deviation from the median, and/or other suitable deviation analysis techniques.

The evaluation of the obtained distal pressure measurements, proximal pressure measurements, and/or ECG traces can include the evaluation of only one of the distal pressure measurements, proximal pressure measurements, and ECG traces, evaluation of two of the distal pressure measurements, proximal pressure measurements, and ECG traces (e.g., the distal and proximal pressure measurements; the distal pressure measurements and ECG traces; or the proximal pressure measurements and ECG traces), or evaluation of all three of the distal pressure measurements, proximal pressure measurements, and ECG traces. Where two or more of the obtained data parameters are evaluated, there is a possibility for one of the parameters to be consistent with a normal heartbeat cycle while another of the parameters indicates an irregular heartbeat cycle. In some implementations, any indication of an irregular heartbeat cycle from the evaluation of any of the parameters results in that heartbeat cycle being considered irregular. However, in other implementations, the parameters are weighted such that an indication of an irregular heartbeat cycle from one parameter may not necessarily result in the heartbeat cycle being considered irregular.

At step 226, the distal pressure measurements and the proximal pressure measurements are optimized based on the evaluation step 224. In that regard, the distal and proximal pressure measurements associated with any heartbeat cycles determined to be irregular are filtered or removed from the data set that will be utilized to evaluate the vessel. Accordingly, the effects of these irregular heartbeat cycles will not adversely affect the subsequent pressure ratio calculations and corresponding evaluation of the vessel lesion(s).

At step 228, a ratio of the optimized distal pressure measurements to the optimized proximal pressure measurements is calculated. The calculated pressure ratio can be the mean, median, and/or mode for all or a subset of the normal heartbeat cycles of the plurality of heartbeat cycles for which data was obtained. Further, in some embodiments the ratio is averaged or stabilized over multiple heartbeat cycles to achieve a desired confidence in the calculation. For example, in some embodiments, the pressure ratio is calculated for two of the normal cardiac cycles and the individual pressure ratio values are averaged. The pressure ratio of a third cycle is then calculated. The average value of the pressure ratios is compared to the average pressure ratio using three cycles. If the difference between the averages is below a predetermined threshold value, then the calculated value is considered to be stable and no further calculations are performed. For example, if a threshold value of 0.001 is used and adding an additional cardiac cycle changes the average pressure ratio value by less than 0.001, then the calculation is complete. However, if the difference between the averages is above the predetermined threshold value, then the pressure ratio for a fourth cycle is calculated and a comparison to the threshold value is performed. This process is repeated iteratively until the difference between the averages of cardiac cycle N and cardiac cycle N+1 is below the predetermined threshold value. As the pressure ratio value is typically expressed to two decimal places of precision (such as 0.80), the threshold value for completing the analysis is typically selected to be small enough that adding a subsequent cardiac cycle will not change the pressure differential value. For example, in some instances the threshold value is selected to be between about 0.0001 and about 0.05.

In some instances, the level of confidence calculation has different thresholds depending on the degree of stenosis and/or an initial calculated pressure ratio. In that regard, pressure ratio analysis of a stenosis is typically based around a cutoff value(s) for making decisions as to what type of therapy, if any, to administer. Accordingly, in some instances, it is desirable to be more accurate around these cutoff points. In other words, where the calculated pressure ratio values are close to a cut-off, a higher degree of confidence is required. For example, if the cutoff for a treatment decision is at 0.80 and the initial calculated pressure ratio measurement is between about 0.75 and about 0.85, then a higher degree of confidence is needed than if the initial calculated pressure ratio measurement is 0.40, which is far from the 0.80 cutoff point. Accordingly, in some instances the threshold value is at least partially determined by the initial calculated pressure ratio measurement.

In some instances, the level of confidence or stability of the calculated pressure ratio is visually indicated to user via a software interface. For example, the color of the calculated pressure ratio may change as the confidence level increases (e.g., fading from a darker color to a brighter color), the user interface may include a confidence scale with a corresponding marker displayed for the particular calculation (e.g., a sliding scale or a bullseye where an indicator of confidence moves closer to the bullseye as confidence increases), the pressure ratio value may transition from a fuzzy or unclear display to a sharp, clear display as confidence increase, and/or other suitable indicators for visually representing the amount of confidence or perceived preciseness of a measurement.

At step 230, the method 220 continues with the calculated pressure ratio being output to a display. The display can be a monitor within a cath lab, a monitor remote from the cath lab, a tablet computer, a handheld computing device, a cell phone, or other suitable display. Further, it is understood that the calculated pressure ratio may be displayed along with other data related to the vessel, including without limitation external images (e.g., angio, CT, MRI, etc.), internal images (IVUS, OCT, spectroscopy, etc.), pressure data (e.g., FFR, iFR, Pa, Pd, etc.), flow data, ECG waveforms, and/or any other relevant vessel or patient information.

Figure 9:
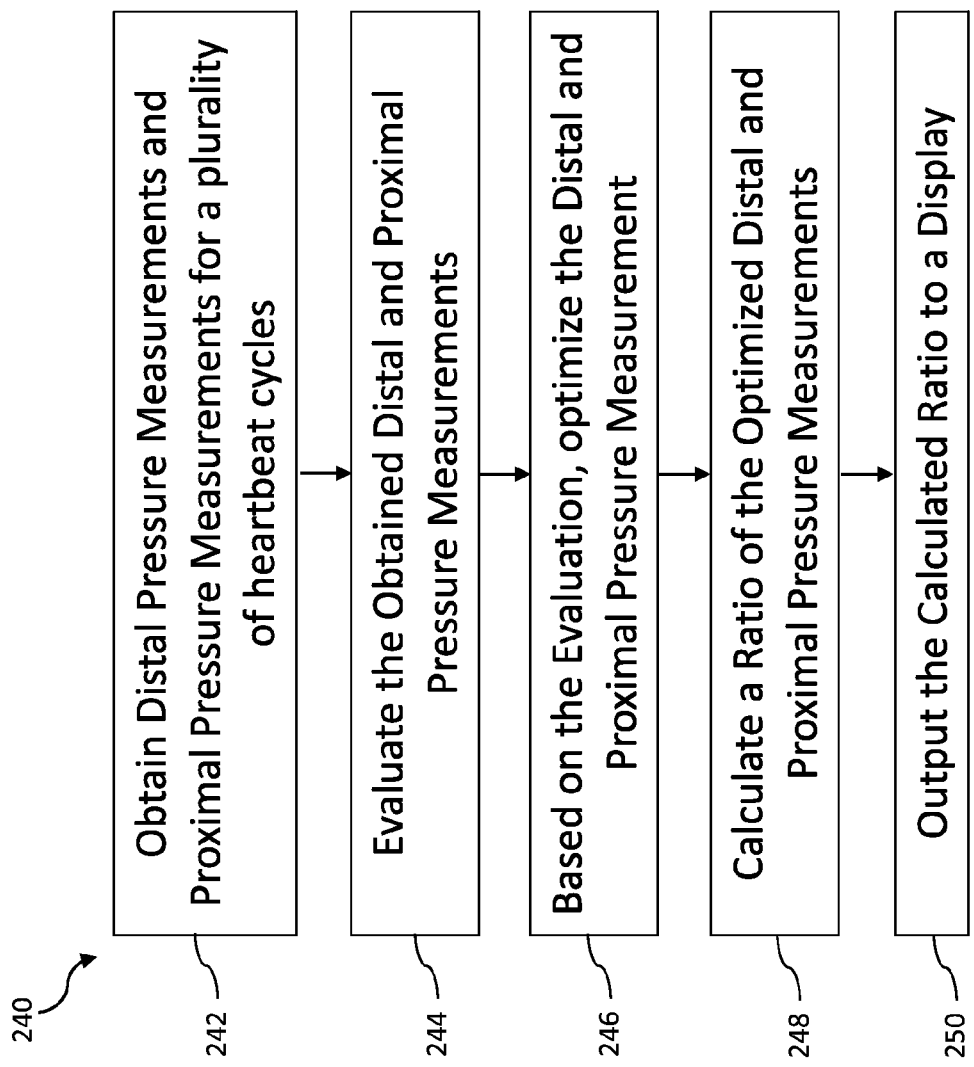
FIG. 9 is a flow chart illustrating steps of a method for evaluating a vessel according to another embodiment of the present disclosure.

Referring now to FIG. 9, shown therein is a flow chart illustrating steps of a method 240 for evaluating a vessel according to an embodiment of the present disclosure. Method 240 is similar in many respects to method 220 described above, but does include the acquisition or evaluation of ECG traces. At step 242, the method begins with obtaining distal pressure measurements and proximal pressure measurements for a plurality of heartbeat cycles. In some implementations, the distal pressure measurements are obtained with a pressure-sensing guidewire, while the proximal pressure measurements are obtained with a pressure-sensing catheter. Further, the distal and proximal pressure measurements can be obtained in real time or on a delayed basis. For example, in some implementations the distal and proximal pressure measurements are obtained during a live procedure. In other instances, the distal and proximal pressure measurements are obtained from a database, hard drive, memory, or other storage device containing data related to a previously performed procedure.

At step 244, the method 240 continues with the evaluation of the obtained distal and proximal pressure measurements. In particular, the obtained distal and proximal pressure measurements are evaluated to identify any irregular heartbeat cycles within the plurality of heartbeat cycles for which data was obtained. In that regard, the irregular heartbeat cycles are identified based on the characteristics of the obtained distal and proximal pressure measurements. Techniques as described in detail above with respect to step 224 of method 220 can likewise be used here and, therefore, will not be repeated for sake of brevity.

At step 246, the distal pressure measurements and the proximal pressure measurements are optimized based on the evaluation step 244. In that regard, the distal and proximal pressure measurements associated with any heartbeat cycles determined to be irregular are filtered or removed from the data set that will be utilized to evaluate the vessel. Accordingly, the effects of these irregular heartbeat cycles will not adversely affect the subsequent pressure ratio calculations and corresponding evaluation of the vessel lesion(s).

At step 248, a ratio of the optimized distal pressure measurements to the optimized proximal pressure measurements is calculated. The calculated pressure ratio can be the mean, median, and/or mode for all or a subset of the normal heartbeat cycles of the plurality of heartbeat cycles for which data was obtained. Further, in some embodiments the ratio is averaged or stabilized over multiple heartbeat cycles to achieve a desired confidence in the calculation.

At step 250, the method 240 continues with the calculated pressure ratio being output to a display. Again, the display can be a monitor within a cath lab, a monitor remote from the cath lab, a tablet computer, a handheld computing device, a cell phone, or other suitable display. Further, it is understood that the calculated pressure ratio may be displayed along with other data related to the vessel, including without limitation external images (e.g., angio, CT, MRI, etc.), internal images (IVUS, OCT, spectroscopy, etc.), pressure data (e.g., FFR, iFR, Pa, Pd, etc.), flow data, ECG waveforms, and/or any other relevant vessel or patient information.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, comprising:
    obtaining proximal pressure measurements associated with blood flow measured at a position proximal of a stenosis of the vessel for a plurality of heartbeat cycles;
    obtaining distal pressure measurements associated with the blood flow measured at a position distal of the stenosis of the vessel for the plurality of heartbeat cycles;
    evaluating the obtained proximal and distal pressure measurements to identify any irregular heartbeat cycles within the plurality of heartbeat cycles;
    optimizing the obtained proximal and distal pressure measurements by removing pressure measurements associated with the irregular heartbeat cycles;
    calculating a pressure ratio between the optimized distal pressure measurements and the optimized proximal pressure measurements; and
    outputting the calculated pressure ratio to a display.

2. The method of claim 1, wherein evaluating the obtained proximal and distal pressure measurements to identify any irregular heartbeat cycles within the plurality of heartbeat cycles includes comparing the obtained proximal and distal pressure measurements to a library of pressure measurements associated with normal heartbeat cycles.

3. The method of claim 1, wherein evaluating the obtained proximal and distal pressure measurements to identify any irregular heartbeat cycles within the plurality of heartbeat cycles includes comparing the obtained proximal and distal pressure measurements for one heartbeat cycle of the plurality of heartbeat cycles to the obtained proximal and distal pressure measurements for other heartbeat cycles of the plurality of heartbeat cycles.

4. The method of claim 1, further comprising:
    obtaining ECG signals for the plurality of heartbeat cycles.

5. The method of claim 4, further comprising:
    evaluating the obtained ECG signals to identify any irregular heartbeat cycles within the plurality of heartbeat cycles.

6. The method of claim 5, wherein evaluating the obtained ECG signals to identify any irregular heartbeat cycles within the plurality of heartbeat cycles includes comparing the obtained ECG signals to a library of ECG signals associated with normal heartbeat cycles.

7. The method of claim 5, wherein evaluating the obtained ECG signals to identify any irregular heartbeat cycles within the plurality of heartbeat cycles includes comparing the obtained ECG signals for one heartbeat cycle of the plurality of heartbeat cycles to the obtained ECG signals for other heartbeat cycles of the plurality of heartbeat cycles.

8. The method of claim 1, wherein the proximal pressure measurements are obtained from a pressure sensing catheter.

9. The method of claim 8, wherein the distal pressure measurements are obtained from a pressure sensing guidewire.

10. The method of claim 1, wherein the calculated pressure ratio is output to the display in real time.

11. A system comprising:
    a processing unit in communication with first and second pressure sensing devices, the processing unit configured to:
        obtain proximal pressure measurements associated with blood flow measured by the first pressure sensing device at a position proximal of a stenosis of a vessel for a plurality of heartbeat cycles;
        obtain distal pressure measurements associated with the blood flow measured by the second pressure sensing device at a position distal of the stenosis of the vessel for the plurality of heartbeat cycles;
        evaluate the obtained proximal and distal pressure measurements to identify any irregular heartbeat cycles within the plurality of heartbeat cycles;
        optimize the obtained proximal and distal pressure measurements by removing pressure measurements associated with the irregular heartbeat cycles;
        calculate a pressure ratio between the optimized distal pressure measurements and the optimized proximal pressure measurements; and
        output the calculated pressure ratio to a display in communication with the processing unit.

12. The system of claim 11, wherein the processing unit is configured to evaluate the obtained proximal and distal pressure measurements to identify any irregular heartbeat cycles within the plurality of heartbeat cycles by comparing the obtained proximal and distal pressure measurements to a library of pressure measurements associated with normal heartbeat cycles.

13. The system of claim 11, wherein the processing unit is configured to evaluate the obtained proximal and distal pressure measurements to identify any irregular heartbeat cycles within the plurality of heartbeat cycles by comparing the obtained proximal and distal pressure measurements for one heartbeat cycle of the plurality of heartbeat cycles to the obtained proximal and distal pressure measurements for other heartbeat cycles of the plurality of heartbeat cycles.

14. The system of claim 11, wherein the processing unit is further configured to:
    obtain ECG signals for the plurality of heartbeat cycles.

15. The system of claim 14, wherein the processing unit is further configured to:
    evaluate the obtained ECG signals to identify any irregular heartbeat cycles within the plurality of heartbeat cycles.

16. The system of claim 15, wherein the processing unit is configured to evaluate the obtained ECG signals to identify any irregular heartbeat cycles within the plurality of heartbeat cycles by comparing the obtained ECG signals to a library of ECG signals associated with normal heartbeat cycles.

17. The system of claim 15, wherein the processing unit is configured to evaluate the obtained ECG signals to identify any irregular heartbeat cycles within the plurality of heartbeat cycles by comparing the obtained ECG signals for one heartbeat cycle of the plurality of heartbeat cycles to the obtained ECG signals for other heartbeat cycles of the plurality of heartbeat cycles.

18. The system of claim 11, wherein the first pressure sensing device is a catheter.

19. The system of claim 18, wherein the second pressure sensing device is a guidewire.

20. The system of claim 11, wherein the processing unit is configured to output the calculated pressure ratio to the display in real time.

* * * * *